(12) United States Patent
Beckert et al.

(10) Patent No.: US 7,438,929 B2
(45) Date of Patent: *Oct. 21, 2008

(54) MULTI-PARTICULATE FORM OF MEDICAMENT, COMPRISING AT LEAST TWO DIFFERENTLY COATED FORMS OF PELLET

(75) Inventors: Thomas Beckert, Warthausen (DE); Hans-Ulrich Petereit, Darmstadt (DE); Jennifer Dressman, Frankfurt (DE); Markus Rudolph, Neu-Isenburg (DE)

(73) Assignee: Roehm GmbH & Co. KG, Darmstadt (DE)

( * ) Notice: Subject to any disclaimer, the term of this patent is extended or adjusted under 35 U.S.C. 154(b) by 614 days.

This patent is subject to a terminal disclaimer.

(21) Appl. No.: 10/949,323

(22) Filed: Sep. 27, 2004

(65) Prior Publication Data

US 2005/0053660 A1 Mar. 10, 2005

Related U.S. Application Data

(63) Continuation of application No. 10/239,209, filed as application No. PCT/EP01/02679 on Mar. 9, 2001, now Pat. No. 6,897,205.

(30) Foreign Application Priority Data

Jan. 31, 2001 (DE) ............................... 101 04 504
Feb. 1, 2001 (DE) ............................... 101 04 880

(51) Int. Cl.
*A61K 9/52* (2006.01)
*A61K 9/14* (2006.01)

(52) U.S. Cl. ........................................ 424/490; 424/489

(58) Field of Classification Search ................. 514/159; 424/489, 490

See application file for complete search history.

(56) References Cited

U.S. PATENT DOCUMENTS

| 4,600,577 A | 7/1986 | Didriksen |
| 4,720,387 A | 1/1988 | Sakamoto et al. |
| 6,897,205 B2 * | 5/2005 | Beckert et al. ............... 514/159 |

OTHER PUBLICATIONS

Schmidt, C., "A Multiparticulate Drug-delivery System Based on Pellets Incorporated into Congealable Polyethylene Glycol Carrier Materials", International Journal of Pharmaceutics 216 (2001) 9-16, Elsevier.*

* cited by examiner

*Primary Examiner*—Johann Richter
*Assistant Examiner*—Danielle Sullivan
(74) *Attorney, Agent, or Firm*—Oblon, Spivak, McClelland, Maier & Neustadt, P.C.

(57) ABSTRACT

The invention relates to a multiparticulate drug form suitable for uniform release of an active pharmaceutical ingredient in the small intestine and in the large intestine, comprising at least two forms of pellets A and B which comprise an active pharmaceutical ingredient in the core and have different polymer coatings which determine the release of the active ingredient at different pH values, characterized in that pellet form A is provided with an inner polymer coating which enables continuous release of active ingredient, and has an outer enteric coating which rapidly dissolves above about pH 5.5, and pellet form B is provided with a polymer coating which, in the USP release test, releases less than 20% of the active ingredient at pH 6.8 in 6 hours and releases more than 50% of the active ingredient at pH 7.2 in 6 hours. The invention additionally relates to a process for producing the multiparticulate drug form and to the use of pellet forms A and B for producing the drug form.

13 Claims, No Drawings

MULTI-PARTICULATE FORM OF MEDICAMENT, COMPRISING AT LEAST TWO DIFFERENTLY COATED FORMS OF PELLET

This is a continuation application of U.S. application Ser. No. 10/239,209 filed on Feb. 12, 2003, which is the national stage of PCT/EP01/02679, filed Mar. 9, 2001.

The invention relates to a multiparticulate drug form which comprises at least two differently coated pellet forms and enables release of active ingredient to be substantially uniform over the entire intestinal region. The invention further relates to a process for producing the multiparticulate drug form and to the use of the pellet forms A and B for producing the drug form.

PRIOR ART

Multiparticulate drug forms obtained by compression of a binder with active ingredient-containing pellets coated with (meth)acrylate copolymers resistant to gastric juice are disclosed in Beckert et al. (1996), "Compression of enteric-coated pellets to disintegrating tablets" *International Journal of Pharmaceuticals* 143, pp. 13-23.

(Meth)acrylate copolymers which comprise monomers with quaternary ammonium groups, e.g. trimethylammoniumethly [sic] methacrylate chloride, and their use for release-slowing medicament coatings have been known for a long time (for example from EP-A 181 515 or from DE-C 1 617 751). Processing takes place in organic solution or as aqueous dispersion, for example by spraying onto medicament cores or else without solvent in the presence of flow aids by application in the melt (see EP-A 0 727 205).

EP-A 629 398 describes pharmaceutical formulations which have a core with an active ingredient and an organic acid, where the core has a two-layer covering. The inner covering in this case is formed by a release-slowing (meth) acrylate copolymer with quaternary ammonium groups (EUDRAGIT® RS), while the outer covering has an enteric coating, for example a copolymer of the type EUDRAGIT® L30D-55 (ethyl acrylate/methacrylic acid, 50:50). The release characteristics achieved can be described by a rapid release of active ingredient after a time lag at elevated pH.

EP 0 704 207 A2 describes thermoplastic materials for drug coverings soluble in intestinal juice. These comprise copolymers of 16 to 40% by weight acrylic or methacrylic acid, 30 to 80% by weight methyl acrylate and 0 to 40% by weight of other alkyl esters of acrylic acid and/or methacrylic acid.

EP 0 704 208 A2 describes coating agents and binders for drug coverings soluble in intestinal juice. These comprise copolymers of 10 to 25% by weight methacrylic acid, 40 to 70% by weight methyl acrylate and 20 to 40% by weight methyl methacrylate. The description mentions not only monolayer coatings but also multilayer coating systems. These may consist of a core which comprises, for example, a basic or a water-sensitive active ingredient, have a sealing layer of another coating material such as cellulose ether, cellulose ester or a cationic polymethacrylate, for example of the EUDRAGIT® type, inter alia including EUDRAGIT® RS and RL, and are then additionally provided with the abovementioned covering soluble in intestinal juice.

Multiparticulate drug forms in the form of capsules or compressed tablets have been known for some time. It is also known to introduce pellets with different polymer coatings into multiparticulate drug forms in order in this way to achieve combined release profiles.

Problem and Solution

There is a need for drug forms which release active ingredients in the intestinal tract and moreover comply with specific active ingredient release profiles.

The intention was to provide a drug form which releases virtually no active ingredient in the stomach and enables release of active ingredient which is as uniform and long-lasting as possible both in the small intestine and in the large intestinal region. The drug form is intended to be suitable for example for the therapy of inflammatory bowel disorders such as ulcerative colitis and, in particular, Crohn's disease.

The object is achieved by a multiparticulate drug form suitable for uniform release of an active pharmaceutical ingredient in the small intestine and in the large intestine, comprising at least two forms of pellets A and B which comprise an active pharmaceutical ingredient in the core and have different polymer coatings which determine the release of the active ingredient at different pH values, characterized in that pellet form A is provided with an inner polymer coating which enables continuous release of active ingredient, and has an outer enteric coating which rapidly dissolves above about pH 5.5, and pellet form B is provided with an inner polymer coating which, in the USP release test, releases less than 20% of the active ingredient at pH 6.8 in 6 hours and releases more than 50% of the active ingredient at pH 7.2 in 6 hours.

The invention further relates to a process for producing a multiparticulate drug form by the different pellet forms A and B being produced by coating active ingredient-containing cores with the stated polymer coatings, being mixed together and being converted into a multiparticulate drug form by introduction into a capsule or compression to a tablet unit in the presence of excipients.

The invention likewise relates to the use of the, described pellet forms A and B in the claimed process for producing a multiparticulate drug form with uniform release of active ingredient in the pH range of 6.8 and [sic] 7.2, corresponding to the conditions in the small and large intestine, in particular for the treatment of Crohn's disease or ulcerative colitis.

MODE OF OPERATION OF THE INVENTION

The multiparticulate drug form may be in the form of a capsule filled with pellets, e.g. a gelatin capsule, or it may be a tablet in which the pellets have been compressed together with conventional excipients to give the tablet unit.

The multiparticulate drug form is suitable for substantially uniform release of an active pharmaceutical ingredient in the small intestine and in the large intestine and comprises at least two forms of pellets, A and B, which comprise an active pharmaceutical ingredient in the core, but have different polymer coatings which determine the release of the active ingredient at different pH values. In vitro, the USP release test (USP 23, method 2) results at pH 6.8 and at pH 7.2 in combined profiles which are between the individual release curves for the two pellet forms A and B. In vivo, the release profile of pellet form A predominates in the small intestine, and release of active ingredient from pellet form B starts while in the large intestinal region.

The pellet cores consist entirely or partly of an active pharmaceutical ingredient. The cores are usually spherical or round and have diameters in the range from about 0.3 to 2 mm. The polymer coatings are in the range from about 2 to 16 mg of polymer per $cm^2$ surface area of the cores.

Pellet form A

Pellet form A is provided with an inner polymer coating and an outer polymer coating.

Inner Polymer Coating

The inner polymer coating enables substantially pH-independent continuous release of active ingredient. The aim is an active ingredient release profile with which, in the USP release test (USP 23, method 2), at pH 6.8 there is about 40 to 70%, preferably 40 to 60%, release of active ingredient after 2 hours, and 60 to 100%, preferably 80 to 100% release after 4 hours. This is derived from the average residence time in the small intestine, which is about 4 hours.

The inner polymer coating of pellet form A may consist of a (meth)acrylate copolymer, of free-radical polymerized $C_1$- to $C_4$-alkyl esters of acrylic or methacrylic acid and (meth) acrylate monomers with a quaternary ammonium group in the alkyl radical.

Appropriate (meth)acrylate copolymers are disclosed, for example, in EP-A 181 515 or DE-C 1 617 751. They are polymers which are soluble or swellable independently of the pH and which are suitable for pharmaceutical coatings. A possible production process to be mentioned is bulk polymerization in the presence of a free-radical initiator dissolved in the monomer mixture. The polymer can likewise also be produced by a solution or precipitation polymerization. The polymer can be obtained in this way in the form of a fine powder, which is achievable in the case of bulk polymerization by grinding, and in the case of solution and precipitation polymerization for example by spray drying.

The (meth)acrylate copolymer is composed of 85 to 98% by weight free-radical polymerized C1- to C4-alkyl esters of acrylic or methacrylic acid and 15 to 2% by weight (meth) acrylate monomers with a quaternary ammonium group in the alkyl radical.

Preferred C1- to C4-alkyl esters of acrylic or methacrylic acid are methyl acrylate, ethyl acrylate, butyl acrylate, butyl methacrylate and methyl methacrylate.

The particularly preferred (meth)acrylate monomer with quaternary ammonium groups is 2-trimethylammonium methyl methacrylate chloride.

A further suitable (meth)acrylate copolymer may be composed, for example, of 85 to less than 93% by weight C1- to C4-alkyl esters of acrylic or methacrylic acid and more than 7 to 15% by weight (meth)acrylate monomers with a quaternary ammonium group in the alkyl radical. Such (meth)acrylate monomers are commercially available and have been used for a long time for release-slowing coatings (type (EUDRAGIT® [sic] RL).

A specifically suitable copolymer comprises, for example, 60% by weight methyl methacrylate, 30% by weight ethyl acrylate and 10% by weight 2-trimethylammoniumethyl methacrylate chloride (EUDRAGIT® RL).

The desired release characteristics can be achieved for example through the thickness of the coating layer of polymer coatings of the "EUDRAGIT® RL type" described above. This is achieved for example with a 5 to 15% coating of EUDRAGIT® RL on active ingredient-containing cores with a diameter of 0.8 to 1.2 mm. The required release characteristics can also be achieved with other layer thicknesses by admixing a copolymer composed of 50-70% by weight methyl methacrylate, 20-40% by weight ethyl acrylate and 7-2% by weight 2-trimethylammoniumethyl methacrylate chloride ("EUDRAGIT® RS type"). A specifically suitable polymer comprises 65% by weight methyl methacrylate, 30% by weight ethyl acrylate and 5% by weight 2-trimethylammoniumethyl methacrylate chloride be composed [sic] (EUDRAGIT® RS). The EUDRAGIT® RL and RS types can be mixed for example in the ratios 10:1 to 1:10. Higher proportions of the "EUDRAGIT® RL type" are preferred, e.g. 60 to 90% by weight in the mixture.

The inner polymer coating may also consist of a (meth) acrylate copolymer composed of 20 to 40% by weight ethyl acrylate and 60 to 80% by weight methyl methacrylate, ethylcellulose or polyvinyl acetate.

Outer Polymer Coating

The outer polymer coating is an enteric coating which rapidly dissolves only above about pH 5.5. The coating is thus intended to prevent release of active ingredient in the substantially [sic] stomach, i.e. this is intended to be no more than 10, preferably only 5, % according to USP 23. On transit into the small intestine it is intended that the outer polymer layer dissolve rapidly so that the release characteristics from this time onwards are determined by the inner polymer coating. If the outer polymer coating is too thin, too much active ingredient is released in the stomach. If the outer polymer coating is applied too thickly, it prevents direct release of active ingredient in the small intestine. Suitable layer thicknesses are, for example, in the range from 15 to 150 μm, preferably, for example, at 20 to 60 μm. Based on the weight of the core provided with the inner polymer coating and having a diameter of from 0.8 to 1.25 mm, it is usually suitable to apply polymer (based on dry matter) in the range from 8 to 40% by weight, preferably from 10 to 25% by weight.

The enteric polymer coating of pellet form A may [lacuna] of a (meth)acrylate copolymer which contains acidic groups and has, for example, acrylic acid, but preferably methacrylic acid, residues.

The (meth)acrylate copolymer consists of 40 to 100, preferably 45 to 99, in particular 85 to 95, % by weight free-radical polymerized $C_1$- to $C_4$-alkyl esters of acrylic or methacrylic acid and may comprise 0 to 60, preferably 1 to 55, in particular 5 to 15, % by weight (meth)acrylate monomers with an anionic group in the alkyl radical.

$C_1$- to $C_4$-alkyl esters of acrylic or methacrylic acid are, in particular, methyl methacrylate, ethyl methacrylate, butyl methacrylate, methyl acrylate, ethyl acrylate and butyl acrylate.

Suitable examples are also neutral (meth)acrylate copolymers of 20 to 40% by weight ethyl acrylate and 60 to 80% by weight methyl methacrylate (EUDRAGIT® NE type) if they are used in a mixture with (meth)acrylate copolymers containing acidic groups.

Particular suitable (meth)acrylate copolymers are composed of 40 to 60% by weight methacrylic acid and 60 to 40% by weight methyl methacrylate or 60 to 40% by weight ethyl acrylate (EUDRAGIT® L or EUDRAGIT® L100-55 types).

Also suitable in principle are anionic (meth)acrylate copolymers of 20 to 40% by weight methacrylic acid and 80 to 60% by weight methyl methacrylate (EUDRAGIT® S type).

Also suitable are (meth)acrylate copolymers consisting of 10 to 30% by weight methyl methacrylate, 50 to 70% by weight methyl acrylate and 5 to 15% by weight methacrylic acid (EUDRAGIT® FS type)

The enteric polymer coating of pellet form A may also consist of shellac, HPMCP (hydroxypropylmethylcellulose phthalate), CAP (cellulose acetate phthalate), HPMC-AS (hydroxypropylmethylcellulose acetate succinate) or polyvinyl acetates [sic] phthalate.

However, care must be taken in every case that the coating is adjusted for example in relation to layer thickness and, where appropriate, mixing with other polymers in such a way that it dissolves rapidly after transit into the small intestine.

Pellet form B

Pellet form B releases, at pH 6.8 in the USP release test (USP 23, method 2), not more than 10%, preferably not more than 5%, after 2 hours and not more than 20, preferably not more than 10, % of the active ingredient after 4 hours. At pH 7.2, about 40 to 60% of active ingredient are released after 3 hours, and about 80 to 100 [lacuna] are released after 60 hours.

The polymer coating for pellet form B may be a (meth)acrylate [sic] copolymer which is composed of 60 to 95% by weight free radical polymerized $C_1$- to $C_4$-alkyl esters of acrylic or methacrylic acid and 5 to 40% by weight (meth)acrylate monomers with an acidic group in the alkyl radical.

Particular suitable (meth)acrylate copolymers consist of 10 to 30% by weight methyl methacrylate, 50 to 70% by weight methyl acrylate and 5 to 15% by weight methacrylic acid (EUDRAGIT® FS type).

Likewise suitable are (meth)acrylate copolymers of 20 to 40% by weight methacrylic acid and 80 to 60% by weight methyl methacrylate (EUDRAGIT® S type).

Pellet form B is preferably provided with only one polymer coating but may, if the release profile in the large intestine is to be modified, also, like pellet form A, be provided additionally with an inner polymer, coating resulting in a substantially pH-independent continuous release of active ingredient. This may be worthwhile if it is necessary to extend the release of active ingredient in the large intestine (colon) to 6 to 12 or up to 24 hours.

Active Ingredients

The formulation of the invention is suitable for the administration of a large number of active pharmaceutical ingredients which are to be released in the small intestine and in the large intestine, and in particular those active ingredients which can advantageously be administered in a slow-release form, such as antidiabetics, analgesics, antiinflammatory agents, antirheumatics, antihypotensive agents, antihypertensive agents, psychoactive drugs, tranquillizers, antiemetics, muscle relaxants, glucocorticoids, agents for treating ulcerative colitis or Crohn's disease, antiallergics, antibiotics, antiepileptics, anticoagulants, antimycotics, antitussives, arteriosclerosis remedies, diuretics, proteins, peptides, enzymes, enzyme inhibitors, gout remedies, hormones and inhibitors thereof, cardiac glycosides, immunotherapeutic agents and cytokines, laxatives, lipid-lowering agents, migraine remedies, mineral products, otologicals, anti parkinson agents, thyroid therapeutic agents, spasmolytics, platelet aggregation inhibitors, vitamins, cytostatics and metastasis inhibitors, phyto-pharmaceuticals, chemotherapeutic agents and amino acids.

Examples of suitable active ingredients are acarbose, antigens, beta-receptor blockers, non-steroidal antirheumatia [sic], cardiac glycosides, acetylsalicylic acid, virustatics, aclarubicin, acyclovir, cisplatin, actinomycin, alpha- and beta-sympatomimetics [sic], (dmeprazole [sic], allopurinol, alprostadil, prostaglandins, amantadine, ambroxol, amlodipine, methotrexate, S-aminosalicylic acid [sic], amitriptyline, amoxicillin, anastrozole, atenolol, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cefalosporins, cetirizine, chenodeoxycholic acid, ursodeoxycholic acid, theophylline and theophylline derivatives, trypsins, cimetidine, clarithromycin, clavulanic acid, clindamycin, clobutinol, clonidine, cotrimoxazole, codeine, caffeine, vitamin D and derivatives of vitamin D, colestyramine, cromoglicic acid, coumarin and coumarin derivatives, cysteine, cytarabine, cyclophosphamide, ciclosporin, cyproterone, cytarabine [sic], dapiprazole, desogestrel, desonide, dihydralazine, diltiazem, ergot alkaloids, dimenhydrinate, dimethyl sulphoxide, dimeticone, dipyridarnoi [sic], domperidone and domperidan [sic] derivatives, dopamine, doxazosin, doxorubizin [sic], doxylamine, dapiprazole [sic], benzodiazepines, diclofenac, glycoside antibiotics, desipramine, econazole, ACE inhibitors, enalapril, ephedrine, epinephrine, epoetin and epoetin derivatives, morphinans, calcium antagonists, irinotecan, modafinil, orlistat, peptide antibiotics, phenytoin, riluzoles, risedronate, sildenafil, topiramate, macrolide antibiotics, oestrogen and oestrogen derivatives, progestogen and progestogen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, fluarizine, fluorouracil, fluoxetine, flurbiprofen, ibuprofen, flutamide, fluvastatin, follitropin, formoterol, fosfomicin, furosemide, fusidic acid, gallopamil, ganciclovir, gemfibrozil, gentamicin, ginkgo, Saint John's wort, glibenclamide, urea derivatives as oral antidiabetics, glucagon, glucosamine and glucosamine derivatives, glutathione, glycerol and glycerol derivatives, hypothalamus hormones, goserelin, gyrase inhibitors [sic], guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramine, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives, evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, oxaceprol, oxacillin, oxiconazole, oxymetazoline, pantoprazole, paracetamol, paroxetine, penciclovir, oral penicillins, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins [sic], protionamide, proxyphylline, quetiapine, quinapril, quinaprilat, ramipril, ranitidine, reproterol, reserpine, ribavirin, rifampicin, risperidone, ritonavir, ropinirole, roxatidine, roxithromycin, ruscogenin, rutoside and rutoside derivatives, sabadilla, salbutamol, salmeterol, scopolamine, selegiline, sertaconazole, sertindole, sertralion [sic], silicates, sildenafil [sic], simvastatin, sitosterol, sotalol, spaglumic acid, sparfloxacin, spectinomycin, spiramycin, spirapril, spironolactone, stavudine, streptomycin, sucralfate, sufentanil, sulbactam, sulphonamides, sulfasalazine, sulpiride, sultamicillin, sultiam, sumatriptan, suxamethonium chloride, tacrine, tacrolimus, taliolol, tamoxifen, taurolidine, tazarotene, temazepam, teniposide, tenoxicam, terazosin, terbinafine, terbutaline, terfenadine, terlipressin, tertatolol, tetracyclins, teryzoline, theobromine, theophylline, butizine, thiamazole, phenothiazines, thiotepa, tiagabine, tiapride, propionic acid derivatives, ticlopidine, timolol, tinidazole, tioconazole, tioguanine, tioxolone, tiropramide, tizanidine, tolazoline, tolbutamide, tolcapone, tolnaftate, tolperisone, topotecan, torasemide, anti-oestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpin, troxerutine, tulobuterol, tyramine, tyrothricin, urapidil, ursodeoxycholic acid [sic], chenodeoxycholic acid [sic], valaciclovir, valproic acid, vancomycin, vecuronium chloride, Viagra, venlafaxine, verapamil, vidarabine, vigabatrin, viloazine, vinblastine, vincamine, vincristine, vindesine, vinorelbine, vinpocetine, viquidil, warfarin, xantinol nicotinate, xipamide, zafirlukast, zalcitabine, zidovudine, zolmitriptan, zolpidem, zoplicone [sic], zotipine and the like.

The active ingredients may, if desired, also be used in the form of their pharmaceutically acceptable salts or derivatives, and in the case of chiral active ingredients it is possible to employ both optically active isomers and racemates or mixtures of diastereo-isomers. If desired, the compositions of the invention may also comprise two or more active pharmaceutical ingredients.

Active ingredients which have been mentioned in particular as suitable for the therapy of ulcerative colitis and Crohn's disease are those which are intended to be released as constantly as possible in the intestine, in particular shortly before or only in the large intestinal region. The active pharmaceutical ingredient may be an aminosalicylate, a sulphonamide or a glucocordicoid and those which should be particularly mentioned are 5-aminosalicylic acid, olsalazine, sulfalazine [sic], prednisone or budesonide. The following table summarizes active ingredients suitable for the therapy of ulcerative colitis and Crohn's disease.

Active Ingredients for the Therapy of Ulcerative Colitis
mesalazine
sulfasalazine
betamethasone 21-dihydrogenophosphate
hydrocortisone 21-acetate
cromoglicic acid
dexamethasone
olsalazine Na
budesonide
bismuitrate, karaya gum
methylprednisolone 21-hydrogensuccinate
prednisone
myhrr, coffee charcoal, camomile flower extract
10% suspension of human placenta
Other Suitable Active Ingredients
balsalazide
orally administered peptides (e.g. RDP 58)
interleukin 6
interleukin 12
ilodecakin (interleukin 10)
nicotine tartrate
5-ASA conjugates (CPR 2015)
monoclonal antibodies against interleukin 12
diethyldihydroxyhomospermine (DEHOHO)
diethylhomospermine (DEHOP)
cholecystokinin (CCK) antagonist (CR 1795)
15 amino acid fragment of a 40 kd peptide from gastric juice (BPC 15)
glucocorticoid analogue (CBP 1011)
natalizumab
infliximab (REMICADE)
N-deacetylated lysoglycosphingolipid (WILD 20)
azelastines
tranilast
sudismase
phosphorothioate antisense oligonucleotide (ISIS 2302)
tazofelones
ropivacaines
5 lipoxygenase inhibitor (A 69412)
sucralfate Administration Forms The described (oral) drug form may be in the form of a tablet made from compressed pellets or in the form of pellets which are packed in a capsule, e.g. composed of gelatin, starch or cellulose derivatives.

Excipients Customary in Pharmacy

Excipients customary in pharmacy can be employed in a manner known per se in the production of the drug form. These excipients may be present in the core or in the coating agent.

Dryers (non-stick agents): Dryers have the following properties: they have large specific surface areas, are chemically inert, are free-flowing and comprise fine particles. Because of these properties, they reduce the tack of polymers containing polar comonomers as functional groups. Examples of dryers are: alumina, magnesium oxide, kaolin, talc, silica (Aerosils), barium sulphate and cellulose.

Release Agents

Examples of release agents are: esters of fatty acids or fatty amides, aliphatic, long-chain carboxylic acids, fatty alcohols and their esters, montan waxes or paraffin waxes and metal soaps; particular mention should be made of glycerol monostearate, stearyl alcohol, glycerol behenic acid ester [sic], cetyl alcohol, palmitic acid, canauba [sic] wax, beeswax, etc. The usual proportionate amounts are in the range from 0.05% by weight to 5, preferably 0.1 to 3, % by weight based on the copolymer.

Other excipients customary in pharmacy: Mention should be made here of, for example, stabilizers, colorants, antioxidants, wetting agents, pigments, gloss agents etc. They are used in particular as processing aids and are intended can be [sic] to ensure a reliable and reproducible production process and good long-term storage stability. Further excipients customary in pharmacy may be present in amounts from 0.001% by weight to 100% by weight, preferably 0.1 to 10% by weight, based on the polymer coating.

Plasticizers: Substances suitable as plasticizers ordinarily have a molecular weight between 100 and 20 000 and comprise one or more hydrophilic groups in the molecule, e.g. hydroxyl, ester or amino groups. Citrates, phthalates, sebacates, castor oil are suitable. Examples of suitable plasticizers are alkyl citrates, glycerol esters, alkyl phthalates, alkyl sebacates, sucrose esters, sorbitan esters, dibutyl sebacate and polyethylene glycols 4000 to 20 000. Preferred plasticizers are tributyl citrate, triethyl citrate, acetyl triethyl citrate, dibutyl sebacate and diethyl sebacate. The amounts used are between 1 and 35, preferably 2 to 10, % by weight % [sic], based on the (meth)acrylate copolymer.

Active Ingredient-Containing Pellets

Active ingredient-containing pellets can be produced by applying active ingredient by means of a layering process. This is done by homogenizing active ingredient together with other excipients (release agents, where appropriate plasticizers) and dissolving or suspending in a binder (e.g.

EUDRAGIT L 30 D-55). A fluidized bed process can be used to apply the liquid to placebo pellets or other suitable carrier materials, with evaporation of the solvent or suspending agent (literature: *International Journal of Pharmaceutics* 143, pp. 13-23). The production process may be followed by a drying step. The active ingredient may be applied in a plurality of layers.

An alternative possibility is to produce active ingredient-containing pellets by an extrusion/spheronization process. This can be carried out for example as follows: lactose (20%) and active ingredient (80%; mesalazine =5-ASA) were mixed in a high speed mixer (DIOSNA type P10, Osnabrück, Germany), and an aqueous solution containing the excipient Kollidon 25 was added in small amounts until a homogeneous composition was obtained. The moist powder mixture was screened. Pellets were subsequently shaped therefrom with the aid of a type 15 Spheronizer (Caleva, Ascot, UK).

The coating with the FS [sic] polymer took place in a Glatt coater (WSG5 or GPCG1 type, Glatt GmbH, Binzen/Lörrach, Germany). A 20% layer (based on dry weight) was applied to the pellets using the top spray method in a manner conventional per se.

Some active ingredients, e.g. acetylsalicylic acid, are commercially available in the form of active ingredient crystals and can be employed in this form in place of active ingredient-containing pellets.

Film coatings of active ingredient-containing pellets are normally applied in fluidized bed equipment. Examples of formulations are mentioned in this application. Film formers are normally mixed with plasticizers and release agents by a suitable process. The film formers may in this case be in the form of a solution or suspension. The excipients for the film formation may likewise be dissolved or suspended. Organic or aqueous solvents or dispersants can be used. Stabilizers can be used in addition to stabilize the dispersion (for example: Tween 80 or other suitable emulsifiers or stabilizers).

Examples of release agents are glycerol monostearate or other suitable fatty acid derivatives, silicic acid derivatives or talc. Examples of plasticizers are propylene glycol, phthalates, polyethylene glycols, sebacates or citrates, and other substances mentioned in the literature.

General conditions for the release tests (e.g. USP 23): pH 1.2: simulated gastric fluid without pepsin (SGF-sp), pH 6.8 and pH 7.2: phosphate buffer complying with DAB 10. ERWEKA type DT 80 apparatus "(paddle) [sic]; 900 ml of test medium at 37° C., 100 rpm. The tests were each carried out in triplicate.

Production of Multiparticulate Drug Forms

The multiparticulate drug form is produced by mixing the different pellet forms A and B. e.g. in the ratio 1:1 or another ratio, depending on the amount of active ingredient present, packing in a capsule or by compression to a tablet unit in the presence of excipients into the multiparticulate drug form.

The production of multiparticulate drug forms by compression of a binder which is customary in pharmacy with active ingredient-containing particles is described in detail for example [lacuna] Beckert et al. (1996) "Compression of enteric-coated pellets to disintegrating tablets", *International Journal of Pharmaceutics* 143, pp. 13-23, and in WO 96/01624.

Mixtures for producing tablets from coated particles are prepared by mixing the pellets with suitable binders for tabletting, if necessary adding disintegration-promoting substances and if necessary adding lubricants. The mixing can take place in suitable machines. Unsuitable mixers are those which lead to damage to the coated particles, e.g. ploughshare mixers. A special sequence of addition of the excipients to the coated particles may be necessary to achieve suitable short disintegration times. Premixing with [sic] the coated particles with the lubricant or mould release agent magnesium stearate is able to render its [sic] surface hydrophobic and thus avoid sticking.

Mixtures suitable for tabletting normally comprise 3 to 15% by weight of a disintegration aid, e.g. Kollidon CL, and e.g. 0.1 to 1% by weight of a lubricant and mould release agent such as magnesium stearate. The binder content is determined by the required content of coated particles.

Typical binders are, for example, Cellactose®, microcyrstalline cellulose, calcium phosphates, Ludipress®, lactose or other suitable sugars, calcium sulphates or starch derivatives. Substances of low bulk density are preferred.

Typical disintegration aids (disintegrants) are cross-linked starch derivatives or cellulose derivatives, and crosslinked polyvinylpyrrolidone. Cellulose derivatives are likewise suitable. The use of disintegration aids may be omitted through selection of a suitable binder.

Typical lubricants and mould release agents are magnesium stearates or other suitable salts of fatty acids or substances detailed in the literature for this purpose (e.g. lauric acid, calcium stearate, talc etc.). The use of a lubricant and mould release agent in the mixture can be omitted if suitable machines (e.g. tablet press with external lubrication) or suitable formulations are used.

The mixture may where appropriate be admixed with an aid to improve flow (e.g. highly disperse silica derivatives, talc etc.).

The tabletting can take place in conventional tablet presses, eccentric or rotary tablet presses, with compressive forces in the range from 5 to 40 kN, preferably 10-20 kN. The tablet presses may be equipped with systems for external lubrication. Special systems for die filling which avoid die filling by means of agitator blades are employed where appropriate.

The application rate means the proportion of dry substance of the functional film-forming polymer sprayed on in % by weight. It is above 15 to 38, particularly preferably 18 to 36, in particular 20 to 30, % by weight based on the particle weight.

The particle content means the weight of the coated particles as a proportion of the total weight of the drug form, the compressed table [sic], in % by weight. The particle content of the drug form is 35-90, particularly preferably 40 to 70, % by weight. Particle contents of from 70 to 90% by weight can be achieved in particular by employing so-called soft cores in place of sugar pellets.

EXAMPLES

Example 1

Pellet Form A, Inner Polymer Coating

Commercially available cores comprising the active ingredient 5-aminosalicylic acid, with a diameter in the range from 0.8 to 1.25 mm, are coated with a 12% coating of a copolymer of 60% by weight methyl methacrylate, 30% by weight ethyl acrylate and 10% by weight 2-trimethylammoniumethyl methacrylate chloride (EUDRAGIT® RL).

For this purpose, 30 g of talc, 12 g of triethyl citrate and 268 g of water are added to 200 g of a 30% strength dispersion of the copolymer (EUDRAGIT® RL 30D) (solids content 20.4 5 [sic]). The cores are coated in a fluidized bed apparatus (STREA 1, Aeromatic-Fielder AG, Bubendorf, Switzerland) with a nozzle arrangement in the bottom-spray mode and a nozzle diameter of 0.8 mm and a spraying pressure of 1.4 to 1.5 bar. 500 g of pellets, air inlet temperature 32-36° C., air outlet temperature 25-30° C., spraying rate 2.4 g/min.

Example 2

Pellet Form A, Outer Polymer Coating

The coated cores from Example 1 are [lacuna] with an outer polymer coating of a (meth)acrylate copolymer of 50% by weight methacrylic acid and 50% by weight ethyl acrylate (EUDRAGIT® L100-55 or Dispersion EUDRAGIT® L 30 D-55)

For this purpose, 25 g of talc, 5 g of triethyl citrate and 204 g of water are added to 166 g of a 30% strength dispersion of the abovementioned copolymer (EUDRAGIT® L30D-55) (solids content 20.4%). The cores are coated as indicated in Example 1 in the fluidized bed apparatus. 20% polymer (polymer dry substance relative to the coated pellet) is applied by spraying.

Example 3

Pellet Form B

Active ingredient-containing pellets are coated as in Example 1 but with a (meth)acrylate copolymer consisting of 25% by weight methyl methacrylate, 65% by weight methyl acrylate and 10% by weight methacrylic acid (EUDRAGIT® FS)

For this purpose, 4 g of glycerol monostearate, 2 g of polysorbate 80, 2.5 g of triethyl citrate and 185 g of water are added to 166 g of a 30% strength dispersion of the abovementioned copolymer (EUDRAGIT® FS 30 D) (solids content of the spray dispersion 20%). The cores are coated as indicated in Example 1 in the fluidized bed apparatus. 20% polymer (polymer dry substance relative to the coated pellet) is applied by spraying.

Example 4

Formula for a multiparticulate drug form composed of pellet forms A and B as in Examples 2 and 3.

| Tablet formulation | |
|---|---|
| Pellet form A | 250.0 g |
| Pellet form B | 250.0 g |
| Cellactose | 417.5 g |
| Kollidon CL | 80.0 g |
| Magnesium stearate | 2.5 g |

The mixture can be compressed to tablets directly in a suitable tablet press using, for example, a compressive force of 15 kN.

The invention claimed is:

1. A multiparticulate drug form comprising at least pellet form A and pellet form B, wherein each of said pellet forms comprises an active pharmaceutical ingredient and at least one polymer coating, wherein the polymer coating of pellet form A is different from the polymer coating of pellet form B, wherein pellet form A comprises an inner polymer coating and an outer enteric coating which rapidly dissolves above about pH 5.5, and pellet form B comprises a different polymer coating which, in the USP release test, releases less than 20% of the active pharmaceutical ingredient at pH 6.8 in 6 hours and releases more than 50% of the active pharmaceutical ingredient at pH 7.2 in 6 hours, wherein said multiparticulate drug form is capable of uniformly releasing the active pharmaceutical ingredient in the small intestine and large intestine, and wherein the polymer coating of pellet form A and pellet form B determines the release of the active pharmaceutical ingredient at different pH.

2. The multiparticulate drug form according to claim 1, wherein the enteric polymer coating of pellet form A comprises an acidic group-containing (meth)acrylate copolymer, shellac, HPMCP (hydroxypropylmethylcellulose phthalate), CAP (cellulose acetate phthalate), HPMC-AS (hydroxypropylmethylcellulose acetate succinate) or polyvinyl acetate phthalate.

3. The multiparticulate drug form according to claim 2, wherein the enteric polymer coating is a (meth)acrylate copolymer comprising 40 to 60% by weight of polymerized methacrylic acid and 60 to 40% by weight of polymerized methyl methacrylate or ethyl acrylate.

4. The multiparticulate drug form according to claim 1, wherein the inner polymer coating of pellet form A comprises a (meth)acrylate copolymer comprising free-radical polymerized $C_1$- to $C_4$-alkyl esters of acrylic or methacrylic acid and (meth)acrylate monomers with a quaternary ammonium group in the alkyl radical, a (meth)acrylate copolymer of 20 to 40% by weight of polymerized ethyl acrylate and 60 to 80% by weight of polymerized methyl methacrylate, ethylcellulose or polyvinyl acetate.

5. The multiparticulate drug form according to claim 4, wherein the inner polymer coating of pellet form A comprises a (meth)acrylate copolymer of 85 to less than 93% by weight of polymerized units of $C_1$- to $C_4$-alkyl esters of acrylic or methacrylic acid and more than 7 to 15% by weight of polymerized (meth)acrylate monomers with a quaternary ammonium group in the ailcyl radical.

6. The multiparticulate drug form according to claim 1, wherein the different polymer coating of pellet form B comprises a (meth)acrylate copolymer comprising 60 to 95% by weight free-radical polymerized $C_1$- to $C_4$-alkyl esters of acrylic or methacrylic acid and 5 to 40% by weight (meth)acrylate monomers with an acidic group in the alkyl radical.

7. The multiparticulate drug form according to claim 6, wherein the different polymer coating of pellet form B comprises a (meth)acrylate copolymer comprising 10 to 30% by weight of polymerized units of methyl methacrylate, 50 to 70% by weight methyl acrylate and 5 to 15% by weight methacrylic acid.

8. The multiparticulate drug form according to claim 6, wherein pellet form B further comprises an inner polymer coating.

9. The multiparticulate drug form according to claim 1, wherein the multiparticulate drug form is capable of uniformly releasing the active ingredient in a pH range of from 6.8 to 7.2.

10. The multiparticulate drug form according to claim 1, wherein the multiparticulate drug form is capable of treating Crohn's disease or ulcerative colitis.

11. The multiparticulate drug form according to claim 1, wherein each of said pellet forms A and B comprise the same active pharmaceutical ingredient.

12. A process for producing the multiparticulate drug form according to claim 1, comprising
- coating cores comprising at least one active pharmaceutical ingredient with an inner polymer coating and an outer enteric coating to form pellet form A,
- coating cores comprising at least one active pharmaceutical ingredient with at least one different polymer coating to form pellet form B,
- mixing said pellet forms A and B, and
- forming the multiparticulate drug form by introducing the mixed pellet forms A and B into a capsule or compressing the mixed pellet forms A and B in the presence of one or more excipients.

13. The process according to claim 12, wherein each of said pellet forms A and B comprise the same active pharmaceutical ingredient.

\* \* \* \* \*